(12) United States Patent
Hargis

(10) Patent No.: US 9,486,352 B2
(45) Date of Patent: Nov. 8, 2016

(54) WRIST SUPPORT DEVICE

(71) Applicant: Calvin Hargis, Warwick, NY (US)

(72) Inventor: Calvin Hargis, Warwick, NY (US)

(*) Notice: Subject to any disclaimer, the term of this patent is extended or adjusted under 35 U.S.C. 154(b) by 419 days.

(21) Appl. No.: 14/029,092

(22) Filed: Sep. 17, 2013

(65) Prior Publication Data

US 2014/0081188 A1  Mar. 20, 2014

Related U.S. Application Data

(60) Provisional application No. 61/702,845, filed on Sep. 19, 2012.

(51) Int. Cl.
| | | |
|---|---|---|
| *A61F 13/04* | (2006.01) | |
| *A61F 5/058* | (2006.01) | |
| *A61F 5/01* | (2006.01) | |

(52) U.S. Cl.
CPC .......... *A61F 5/05866* (2013.01); *A61F 5/0118* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,782,825 A | * | 11/1988 | Lonardo | A61F 5/05866 602/21 |
| 5,672,150 A | * | 9/1997 | Cox | A61F 5/0118 128/879 |
| 5,921,945 A | * | 7/1999 | Gray | A61F 5/0585 128/882 |
| 6,120,472 A | | 9/2000 | Singer, Jr. | |
| 2002/0052568 A1 | | 5/2002 | Houser et al. | |
| 2003/0125652 A1 | * | 7/2003 | Porrata | A61F 5/0118 602/21 |
| 2004/0133137 A1 | | 7/2004 | Hargis | |

* cited by examiner

*Primary Examiner* — Ophelia A Hawthorne
(74) *Attorney, Agent, or Firm* — Howson & Howson, LLP

(57) ABSTRACT

A wrist support device includes a splint body having a central portion and a thumb extension. The central portion provides a protective shield which is located such as to overlie a carpal tunnel of a human wrist when the device is worn. The central portion is raised relative to surrounding sections of the splint body such that the central portion can be elevated from the carpal tunnel, does not contact the wearer, and provides a support surface which disperses external forces acting thereon to locations other than the carpal tunnel so as not to compress the carpal tunnel. The thumb extension section of the splint body confronts, supports and stabilizes a base of a thumb of the wearer. The device permits the wearer to rest the inner wrist on counters, keyboard surfaces, counter edges or sharp and irregular surfaces without compression of the carpal tunnel area.

11 Claims, 4 Drawing Sheets

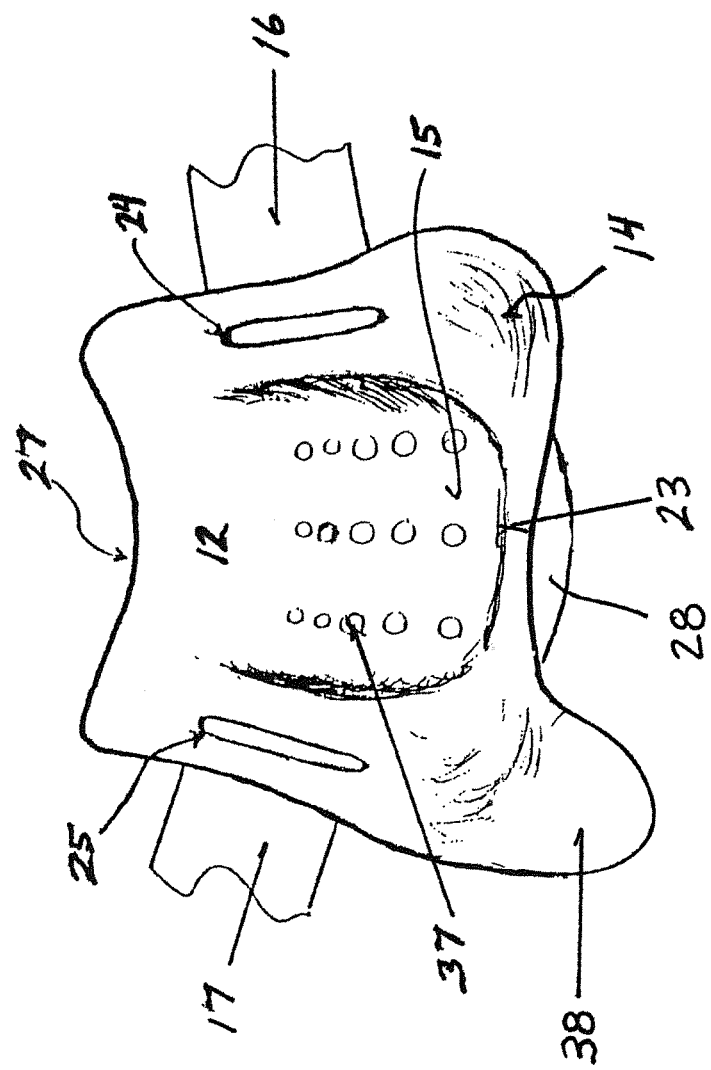

WRIST SUPPORT DEVICE

CROSS REFERENCE TO RELATED APPLICATIONS

This application claims the benefit under 35 USC §119(e) of U.S. Provisional Patent Application No. 61/702,845, filed Sep. 19, 2012.

BACKGROUND

Carpal tunnel syndrome is a condition of the hand caused by direct compression, bruising and swelling of the synovial membranes, tendons and nerves of the carpal tunnel region, and by any condition that reduces the available space in the carpal tunnel.

Prolonged compression of the inner wrist from many consecutive hours of resting the wrist on hard or irregular surfaces can lead to over-compression of the carpal tunnel and its median and ulnar nerves. In addition, excessive flexion of the wrist and fingers, such as repetitive and forceful grasping of the hands and repetitive bending of the wrist, are common causes of carpal tunnel syndrome. Carpal tunnel syndrome can also be caused from injury or trauma such as blunt contusions, wrist bone dislocations and fractures which compromise the carpal tunnel, thereby resulting in pressure on the median nerve.

Common symptoms of carpal tunnel syndrome include pain and numbness of the hand and fingers. These symptoms are worsened by the confined nature of the carpal tunnel itself being bounded by carpal bones at its dorsal aspect and by dense fibrous tissue of the transverse carpal ligament at its volar aspect leaving little room for the delicate carpal nerves.

Treatment of carpal tunnel syndrome varies according to the severity of the condition. Severe conditions usually require hand surgery to sever the transverse carpal ligament. For less severe cases, the use of a splint, which immobilizes the wrist, is sometimes effective, often in combination with anti-inflammatory medication. Such treatments are generally expensive, painful and may reduce the patient's ability to use the affected hand.

BRIEF DESCRIPTION OF THE DRAWINGS

FIG. 4 is a view of an underside of a wrist supporting device in accordance to an embodiment.

DETAILED DESCRIPTION

Figure 1:
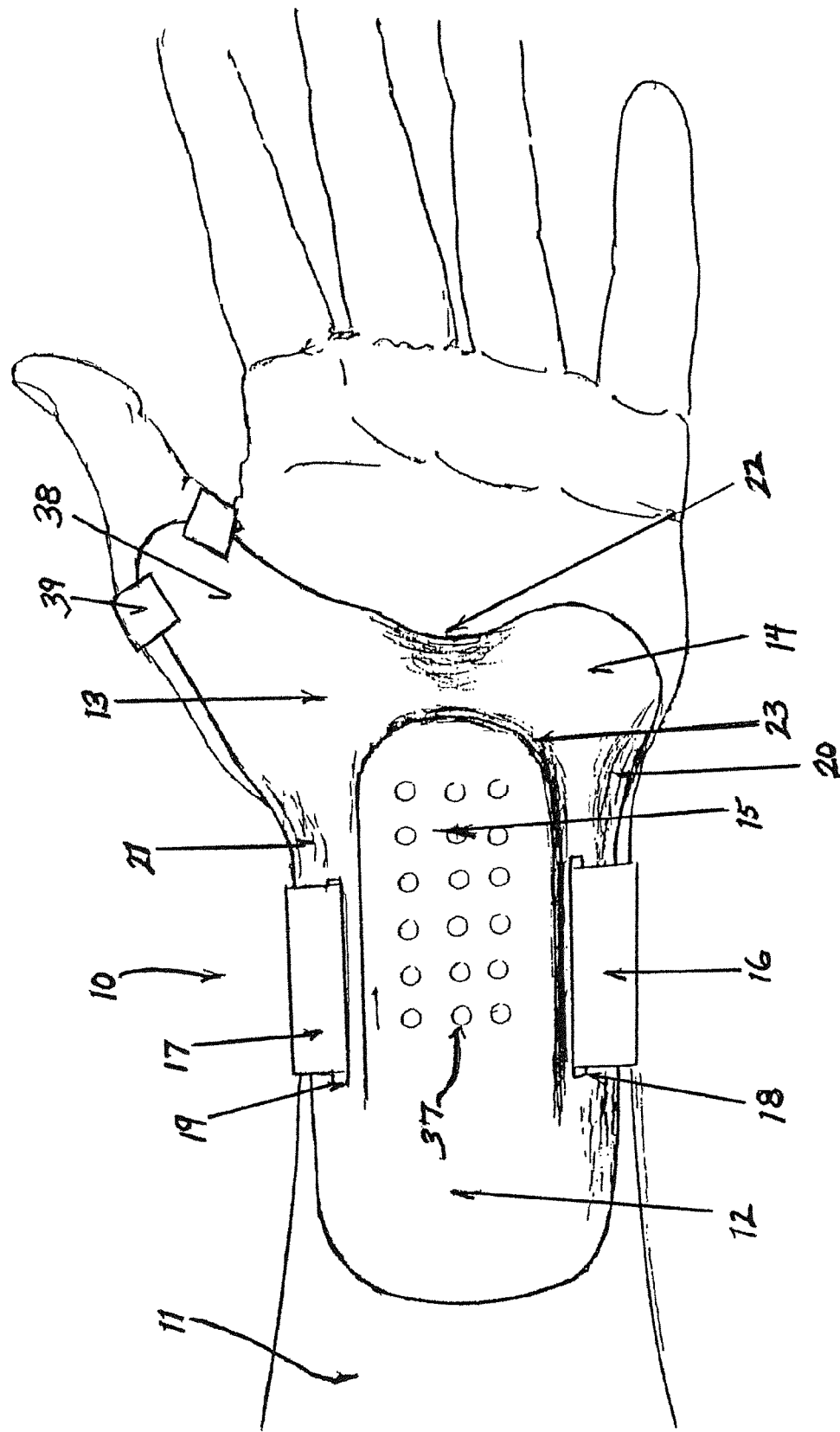
FIG. 1 is a front view of a wrist support device in operating position attached to a wearer in accordance to an embodiment.

The present invention relates to a device, brace, splint or the like for preventing and alleviating carpal tunnel syndrome. In particular, the device attaches at the wrist of a wearer and can be used to support the wrist and hand on an underlying surface such that the hand and wrist are disposed at about a 10 degree angle relative to the horizontal. Such a position is hereinafter referred to as a neutral position. While worn, the device allows the wearer free motion of the wrist in directions unrelated to carpal tunnel syndrome, full use of the hand and digits of the hand, and a greater degree of comfort than provided in prior wrist support devices, such as supports, splints, braces, gloves, bracelets and the like.

Carpal tunnel syndrome is particularly a problem for workers in industries which require repeated manual hand motions and prolonged postures of resting the inner wrists to hard surfaces. Devices such as keyboard wrist rests have been used but tend to provide little benefit and in fact may promote problems as they allow the weight of the hand and forearm to be rested centrally atop the carpal tunnel area applying pressure thereto.

Wrist devices that have been used for the treatment or prevention of carpal tunnel syndrome typically impede free motion of the hand and digits of the hand, are uncomfortable to wear, do not prevent the wrist from dropping below the neutral position, are cumbersome, can become snagged on sharp or hooked objects, are difficult to remove and re-apply, and tend to be heavy. Conventional wrist devices also permit the volar wrist and carpal tunnel region to come into contact with the inner aspect of the brace itself and thereby transfer pressure from the resting surface through the brace to the carpal tunnel space. In addition, bracelets, gloves and the like create circumferential pressure points around the wrist, and although touted to alleviate carpal tunnel syndrome, create added compression of the carpal tunnel region due to application of circumferential pressure that can be uncomfortable to the wearer. This is especially true of elastomeric gloves that generate circumferential forces that pressurize the carpal tunnel while worn. Still further, conventional wrist supports that enclose the wrist and at least portions of the hand unnecessarily restrict hand mobility and are uncomfortable to wear. Although braces may be adapted to hold the carpal area, wrist, hand and forearm in a fixed or semi-fixed alignment, conventional braces typically contact the carpal tunnel on the inner aspect of the brace allowing for the transmittal of arm pressure through the brace to the delicate carpal tunnel region.

Accordingly, the present invention relates to a device for supporting a wrist, and more particularly, to a wrist support device used for abating the effects of sustained or intermittent pressure to the carpal tunnel from sharp, irregular or heavy objects that compress the carpal tunnel area and lead to carpal tunnel syndrome. In addition, the wrist support device of the present invention provides weight dispersal to less sensitive portions of the hand and forearm while sparing compression to the delicate carpal tunnel region.

The wrist support device disclosed herein can be used for the treatment and prevention of carpal tunnel syndrome and, when worn, can maintain the wrist and hand in a relatively neutral position when the wrist is rested on an underlying surface. An embodiment of the wrist support device disclosed herein does not unduly impede movement and use of the hand and at least selected digits thereby facilitating ease of work and productivity. Additionally, the wrist support device protects the carpal tunnel allowing no compression what so ever to the area from flat, sharp, irregular or heavy objects and thereby transfer force, weight and pressure to less sensitive portions or the hand/forearm where delicate nerves are not prone to compression. Further, the wrist support device is comfortable to wear, lightweight, and unlikely to become caught or snagged on sharp or projecting objects.

One embodiment of a wrist support device 10 according to the present invention is shown in FIGS. 1-4. The device 10 includes a single thin integral splint body that can be made of plastic or like rigid or semi-rigid, lightweight material. As an alternative, the body of the device 10 can be made of an elastomeric or rubber material having a degree of elasticity and flexibility. In addition, padding may be added to an underside of the device 10 at locations where the device 10 contacts the wearer. In all cases, as will be discussed, the body is sufficiently rigid to hold its intended shape and to not collapse such as to permit direct contact of the device with the carpal tunnel area of the wearer. For purposes of example, the body can be manufactured form a single integral thin sheet of plastic or thermoplastic material that is molded into the contour shown in FIGS. 1-4. The thickness of the thin sheet may be about 1/16 inch, and the device 10 may weight about only 1.5 to 2 ounces.

The integral body of the device 10 has the following sections: (i) a palmar section including sections 13 and 14; (ii) a main or mid-section comprising sections 15, 20 and 21; (iii) a tail end section 12; and (iv) a thumb extension section 38. When the device 10 is worn, the palmar section, 13 and 14, is intended to confront and cup the heel of the wearer's hand, the main or mid-section, 15, 20 and 21, extends from the palmar section, 13 and 14, to the tail end section 12 which is intended to confront the wearer's forearm 11, and the thumb extension section 38 extends forward from the palmar section 13 to confront, support and stabilize the base of the wearer's thumb. For purposes of securing the device 10 to the wearer's wrist and to thumb, straps 16, 17 and 39 or the like can be provided.

The palmer section, 13 and 14, contacts, engages, fits, and cups the heel of a wearer's hand at the thenar and hypothenar eminences, respectively. More specifically, the palmar section 13 extends over the heel of the hand at the thenar eminence where it contours, fits and cups the shape of this anatomic area. As will be discussed in greater detail, the thumb extension section 38 extends from the palmar section 13. The palmar section 14 tapers forward and extends at least partially over the heel of the hand at the hypothenar eminence where it contours, fits and cups the shape of this anatomic area. The sections 13 and 14 are connected by a portion 22 that contours the mid area of the palm between the thenar and hypothenar regions. The sections 13 and 14 have sufficient width to provide support for the center of the thenar and hypothenar eminences thereby displacing the weight of a resting arm and hand away from the carpal tunnel and to the heel of the palm.

The main or mid-section of the device 10 as provided by outer portions 20 and 21 and central portion 15 extend rearward from the palmar section, 13 and 14, a length sufficient to extend across the wrist and carpal tunnel area and beyond the carpal tunnel area. The main or mid-section of the device 10 is of a shape whereby direct contact of the device 10 with the wearer is restricted to engagement only with specific locations of the forearm of the wearer, more specifically, lateral locations on the forearm (i.e., lateral of the carpal tunnel area).

In the illustrated embodiment, the outer portions 20 and 21 of the main or mid-section of the device 10 have a narrowed and contoured area at the wrist-hand junction of the wearer for contacting the lateral wrist just outside of the carpal tunnel area and extend partially along the forearm of the wearer. In contrast, the central portion 15 of the main or mid-section of the device 10 has the form of a raised or domed area that is intended to provide a shield to the carpal tunnel region and to prevent contact with and compression of the carpal tunnel region of the wearer by external objects as well as the central portion 15 itself. The width of the central portion 15 of the main or mid-section of the device 10 is sufficient to permit outer portions 20 and 21 to comfortably cradle the lateral forearm of the wearer. When the device is worn, the central portion 15 may be elevated above and away from the width and breath of the carpal tunnel area of the wearer by approximately five millimeters at the forward aspect thereof and may taper in a rearward direction gradually to conform with and to lie against the forearm at the rearward or proximal border of the carpal tunnel area at the forearm 11 at the tail end section 12 of the device 10.

Figure 2:
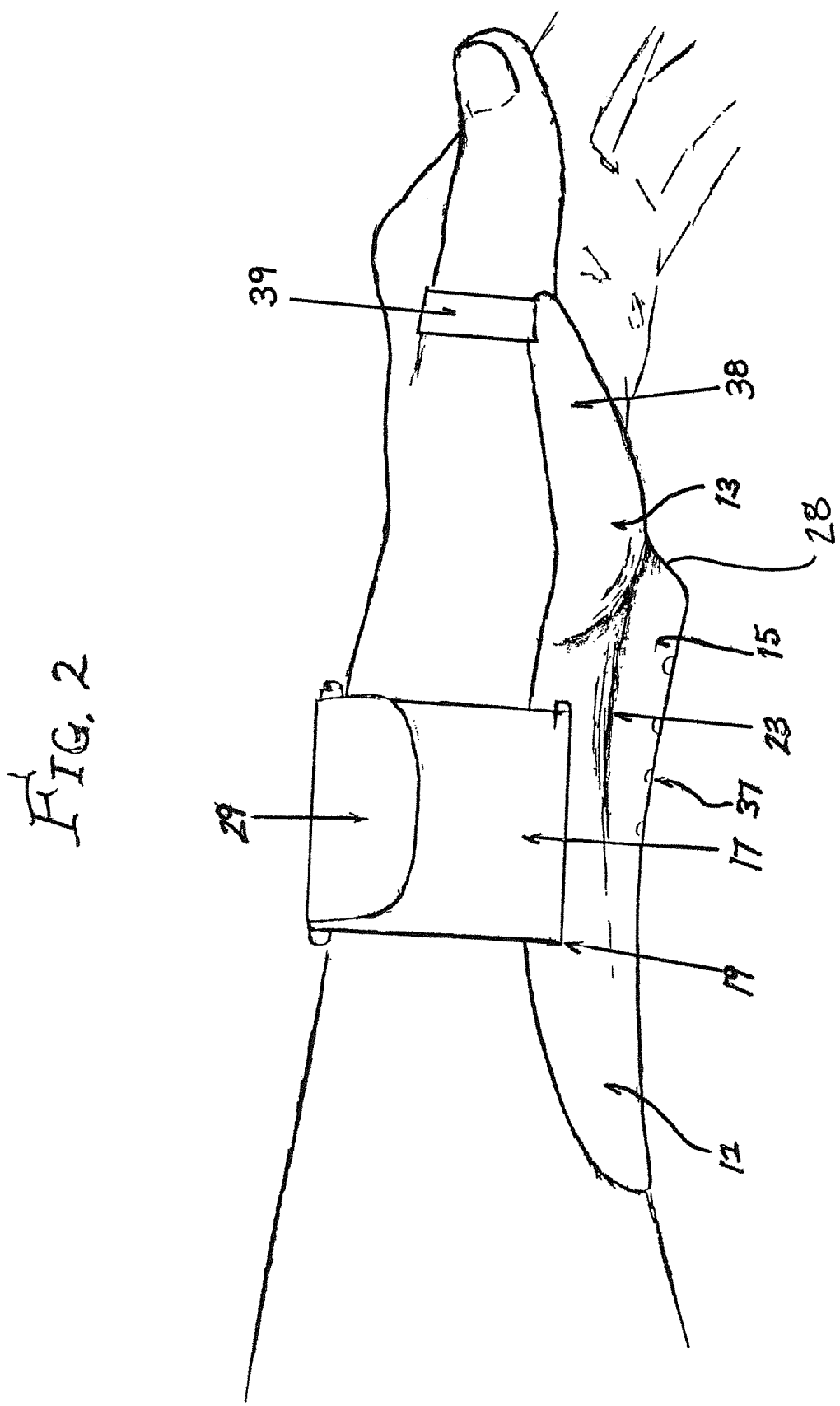
FIG. 2 is a side view of a wrist support device in operating position attached to a wearer in accordance to an embodiment.

As best illustrated in FIG. 2, the central portion 15 can have a relative planar or flat surface providing the wrist in the neutral position when the device 10 is rested on an underlying object or edge. In this position, nothing contacts or can compress the carpal tunnel region. The raised portion 15 can be shaped to curve downward and outward to contact the proximal base of the hand just forward of the mid wrist crease (see portion 28 best shown in FIGS. 2 and 4), laterally the outer borders of the volar wrist just outside the lateral borders of the anatomic carpal tunnel, and rearward the forearm just proximal to the anatomic carpal tunnel area. In addition, the raised central portion or dome 15 of the main or mid-section of the device 10 may have ventilation openings 37 and a contoured margin 23 at the border of the raised central portion or dome 15 which demarcates the area where the sides of the raised dome elevate away from the lateral margins of outer portions 20 and 21. Slots 18 and 19 or the like may be formed in the outer portions 20 and 21 for passage of the wrist straps 16 and 17 to connect the straps 16 and 17 to the device 10.

The wrist support device 10 may also include a thumb and/or digit extension. In the embodiment shown in FIG. 1, the device 10 includes a thumb extension section 38 that extends from the palmar section 13. Accordingly, when the device 10 is worn, the thumb extension section 38 confronts, contacts, supports and stabilizes the base of the thumb of the wearer as shown in FIGS. 1 and 2. A strap 39 connects to the thumb extension section 38 and encircles the base of the thumb for purposes of securing the thumb of the wearer to the thumb extension section 38.

The thumb extension section 38 of device 10 restricts movement of the wearer's thumb thereby allowing a degree of immobilization of the thumb without the need of a cast. However, the wearer can still make use of the hand, and the device 10 makes it possible to accomplish work such as typing on a keyboard with the hand and thumb while treating and preventing carpal tunnel syndrome. In particular, by restricting the thumb, the wrist support device 10 provides immobilization to aid resolution of several conditions, including: (i) a strain/sprain of the joint and surrounding tissue of the $1^{st}$ metacarpal/phalangeal joint (i.e., the joint at the base of the thumb); (ii) tenosynovitis (inflammation) of tendons at the base of the thumb known as DeQuervain's disease; and (iii) osteoarthritis of the joint.

Although the illustrated embodiment shows the wrist support device 10 having a thumb extension section 38 for stabilizing and supporting the base of a wearer's thumb, other contemplated embodiments of a wrist support device include additional extensions (not shown) for supporting and stabilizing at least the base of one or more other digits of the hand.

Figure 3:
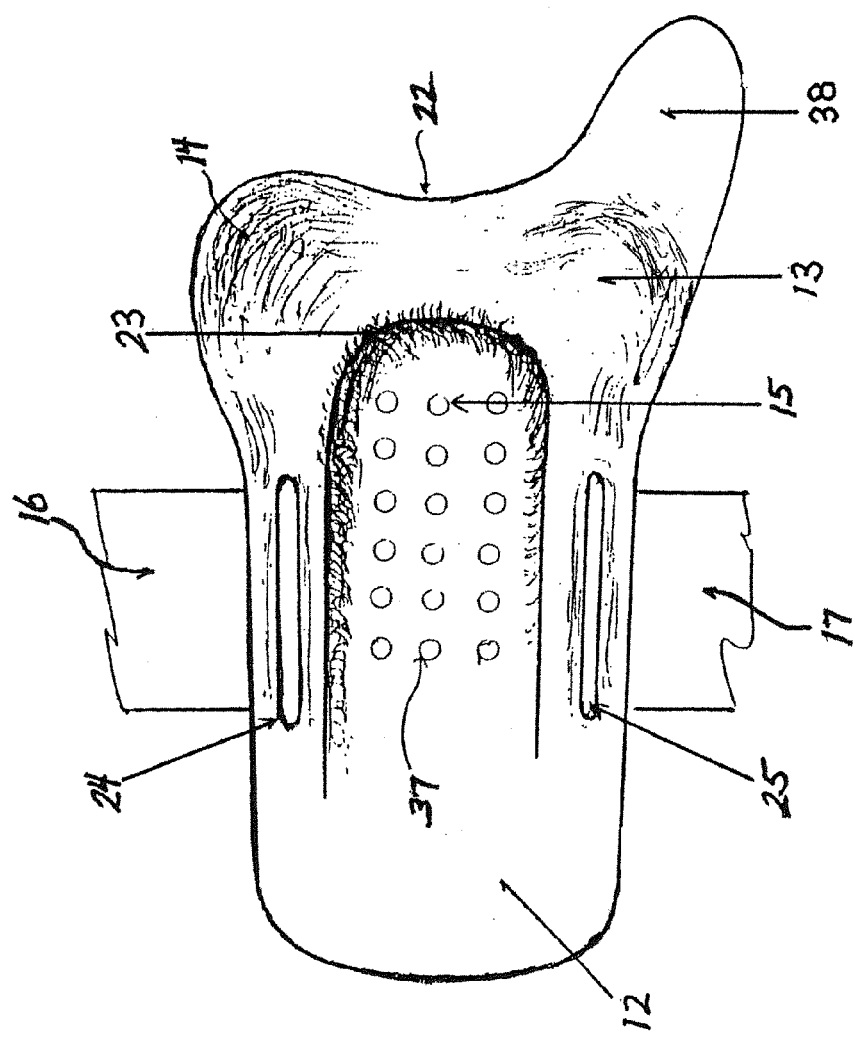
FIG. 3 is a view of an underside of a wrist supporting device in accordance to an embodiment.

FIGS. 3 and 4 provide views showing the underside of the wrist support device 10 when not secured to a wearer. These views show the general contour of the contacting areas of the device 10 to the wearer. A rim 23 of the central portion 15 of the device 10 provides a demarcation where a cavity is formed thereby permitting the central portion 15 to be raised or elevated relative to the carpal tunnel area of the wearer when the device 10 is worn. Areas 24 and 25 are terminal areas of the straps 16 and 17 where the straps pass through the slots 18 and 19. The terminal ends 24 and 25 of the straps 16 and 17 are made large enough to prevent their passing through the slots 18 and 19. It should be understood that straps 16 and 17 would extend to be fastened atop the wrist and forearm by any convention means such as hook-and-loop style fasteners, buckles, snaps, or the like.

As best shown in FIG. 4, the sections 13 and 14 of the device correspond to the thenar and hypothenar areas of the hand of the wearer are curved as previously described to contour the above referenced eminences. The thumb extension section 38 extends a distance forward of both the sections 13 and 14. The tail end section 12 of the device 10 includes a rear edge 27.

Accordingly, the wrist support device 10 can be used to prevent compression of the carpal tunnel region of the wearer and can be used to alleviate and prevent carpal tunnel syndrome. The wrist support device 10 can be worn to maintain the hand at the neutral position, support the hand at a proper keyboard typing height, to not unnecessarily restrict movement of the hand and at least selected digits of the hand which are unrelated to carpal tunnel syndrome, and to prevent compression either externally from work surfaces or internally from brace components to the delicate area of the carpal tunnel as a result of external or internal forces acting upon the wrist and hand. In addition, the wrist support device 10 provides immobilization to the thumb to aid resolution of several conditions, including: (i) a strain/sprain of the joint and surrounding tissue of the $1^{st}$ metacarpal/phalangeal joint (i.e., the joint at the base of the thumb); (ii) tenosynovitis (inflammation) of tendons at the base of the thumb known as DeQuervain's disease; and (iii) osteoarthritis of the joint.

During normal operation, the wrist support device 10 can be positioned across the wrist of the wearer to support the hand and wrist in the neutral position while restricting hand flexion slightly and while immobilizing the base of the thumb. The device 10 is sized to span a proximal palm of the wearer, the base of the thumb of the wearer, a volar surface of the wrist of the wearer, and a proximal forearm of the wearer. While worn, the device allows the wearer free motion of the wrist in all other directions not conducive to carpal tunnel syndrome, full use of the hand and at lease selected ones of the digits of the hand, and a degree of comfort. The raised central part 15 or dome of the device 10 extends above the carpal tunnel area and functions to prevent any pressure to the area and to allow for the displacement of weight away from that area to the palm, lateral wrist and proximal forearm. Thus, the wearer may rest his or her hand and forearm upon hard, sharp or irregular or pointed surfaces and projections for prolonged periods without compression of the carpal tunnel region. Additionally the wearer cannot compress the carpal tunnel even in positions of extreme wrist extension. Further, the device 10 is extremely easy to remove or re-attach, and the wearer may adopt sleeping positions wherein the head is placed atop the hand and wrist without transmitting the weight of the head to the carpal tunnel to compress and injure the carpal tunnel area.

The foregoing description and specific embodiments are merely illustrative of the principles thereof, and various modifications and additions may be made to the apparatus by those skilled in the art, without departing from the spirit and scope of this invention.

The invention claimed is:

1. A wrist support device, comprising:
a splint body having a palmar section, a mid-section including a central portion, a tail end, and a thumb extension section, said splint body, when worn on a human wrist, permitting free movement of the wrist of a wearer and being sized to span a proximal palm of the wearer, a base of the thumb of the wearer, a volar surface of the wrist of the wearer, and a proximal forearm of the wearer, and said splint body being self-supporting in shape, weighing 1.5 to 2 ounces, and being sufficiently rigid so as to maintain shape and support characteristics under load bearing; and
a strap extending from said thumb extension section of said splint body for removably securing said thumb extension section of said splint body to the base of the thumb of the wearer;
said palmar section of said splint body being contoured to fit and cup rounded surfaces of thenar and hypothenar areas of the palm of the wearer;
said thumb extension section extending integrally from and forwardly of said palmar section to confront, support and stabilize the base of the thumb of the wearer;
said mid-section extending from and rearward of said palmar section to said tail end and having a contour to engage the forearm of the wearer beyond the carpal tunnel of the human wrist, said mid-section including outward portions that have a contour that comfortably cradle the forearm of the wearer at locations along the wrist lateral of the carpal tunnel such that, when the device is worn by the wearer, said palmar section contacts the proximal base of the hand of the wearer adjacent and forward of a mid-wrist crease of the wearer, said outer portions of said mid-section are configured to contact the wearer at locations lateral of the volar wrist adjacent outside lateral borders of the carpal tunnel, and said tail end section is configured to contact the wearer rearward of the forearm proximal to the carpal tunnel;
said central portion being planar and providing a protective shield which is located such as to overlie the carpal tunnel of the human wrist when the device is worn, said central portion being raised relative to surrounding sections of the splint body such that, when the device is worn, the central portion is elevated from the carpal tunnel of the human wrist, does not contact the wearer, and provides a flat exterior support surface which disperses any external forces acting thereon to locations other than the carpal tunnel of the human wrist so as not to compress the carpal tunnel;
said mid-section sloping downward from lateral edges of said planar central portion to said outer portions configured to contact the wrist and support the central portion a predetermined height above the wrist of the wearer and forms a hollow cavity beneath said central portion, said hollow cavity is configured to extend over the carpal tunnel area of the human wrist such that said central portion is elevated above and away from a width and breath of the carpal tunnel of the human wrist by approximately five millimeters; and
said central portion being perforated for ventilating the hollow cavity and the wearer's skin.

2. A wrist support device according to claim 1, wherein said splint body is made from a single integral piece of material.

3. A wrist support device according to claim 2, wherein said splint body is made from a plastic or thermoplastic material.

4. A wrist support device according to claim 2, wherein said splint body is made of an elastomeric material.

5. A wrist support device according to claim 1, wherein said thumb extension section is made of a rigid material.

6. A wrist support device according to claim 1, further comprising at least one wrist strap extending from the device for securing the device to the human wrist, said wrist strap extending from said outer portions of said mid-section and does not extend completely about the wrist of the wearer.

7. A wrist support device, consisting of:
a single, integral, elongate, splint body having a palmer section, a mid-section, a tail end section and a thumb extension section, said splint body, when worn on a human wrist, permitting free movement of the wrist of a wearer and being sized to span a proximal palm of the wearer, a base of the thumb of the wearer, a volar surface of the wrist of the wearer, and a proximal forearm of the wearer, and said splint body being self-supporting in shape, weighing 1.5 to 2 ounces, and being sufficiently rigid so as to maintain shape and support characteristics under load bearing;
a wrist strap connected to said mid-section of said splint body for securing said splint body to a human wrist, said wrist strap extending from opposite edge portions of said mid-section and does not extend completely about the wrist of the wearer; and
a thumb strap connected to said thumb extension section of said splint body for securing said thumb extension section to the base of the thumb of the wearer;
said mid-section including a central portion that is planar and provides a protective shield which is located such as to overlie a carpal tunnel of the human wrist when the device is worn, said central portion being raised relative to surrounding sections of the splint body such that, when the device is worn, the central portion is elevated from the carpal tunnel of the human wrist, does not contact the wearer, and provides a flat exterior support surface which disperses any external forces acting thereon to locations other than the carpal tunnel of the human wrist so as not to compress the carpal tunnel;
said mid-section forming a hollow cavity beneath said central portion, said hollow cavity is configured to extend over the carpal tunnel area of the human wrist such that said central portion is elevated above and away from a width and breath of the carpal tunnel of the human wrist by about five millimeters; and
said central portion being perforated for ventilating the hollow cavity and the wearer's skin.

8. A wrist support device according to claim 7, wherein said palmar section is contoured to fit and cup rounded surfaces of thenar and hypothenar areas of a palm of the wearer, and wherein said thumb extension section extends integrally from and forwardly of said palmar section to confront, support and stabilize the base of the thumb of the wearer.

9. A wrist support device according to claim 8, wherein said mid-section is configured to extend from and rearward of said palmar section to said tail end of said splint body, wherein said tail end section has a contour for engaging a forearm of the wearer beyond the carpal tunnel of the human wrist, and wherein said mid-section includes outward portions that have a contour that is configured to cradle the forearm of the wearer at locations along the wrist lateral of the carpal tunnel.

10. A wrist support device according to claim 9, wherein said mid-section includes slopes which slope downward from lateral edges of said central portion to said outer portions configured to contact the wrist and support the central portion above the wrist of the wearer.

11. A wrist support device according to claim 10, wherein said splint body is made of an elastomeric material.

* * * * *